United States Patent [19]
Cox

[11] Patent Number: 5,074,292
[45] Date of Patent: Dec. 24, 1991

[54] CONFORMABLE BRACE AND METHOD OF APPLICATION

[76] Inventor: Michael F. Cox, 3499 Oaks Way, Pompano Beach, Fla. 33069

[21] Appl. No.: 668,680

[22] Filed: Mar. 7, 1991

Related U.S. Application Data

[63] Continuation of Ser. No. 562,451, Aug. 1, 1990, abandoned, which is a continuation of Ser. No. 210,325, Jun. 23, 1989, abandoned.

[51] Int. Cl.$^5$ .............................................. A61F 5/04
[52] U.S. Cl. ...................................... 128/90; 128/77; 128/78; 128/80 R; 128/878; 128/882
[58] Field of Search ............... 128/77, 78, 80 R, 80 C, 128/87 R, 89 R, 90, 96, 869, 870, 878, 879, 881, 882

[56] References Cited

U.S. PATENT DOCUMENTS

| | | | |
|---|---|---|---|
| 3,680,548 | 8/1972 | Brown | 128/90 X |
| 3,871,367 | 3/1975 | Miller | 128/78 |
| 4,006,741 | 2/1977 | Arluck | 128/90 |
| 4,173,973 | 11/1979 | Hendricks | 128/78 |
| 4,508,110 | 4/1985 | Modglin | 128/78 |
| 4,541,419 | 9/1985 | Osawa | 128/78 |
| 4,572,167 | 2/1986 | Brunswick | 128/78 |
| 4,600,618 | 7/1986 | Raychok, Jr. et al. | 128/90 X |
| 4,852,556 | 8/1989 | Groiso | 128/87 R |

OTHER PUBLICATIONS

"Lucite ®L" Brochure, Du Pont Co. 4/1988.
"Acrylic Resins", *Handbook of Plastics* by Simonds et al., Second Edition, 1949, pp. 277-281.

*Primary Examiner*—Edgar S. Burr
*Assistant Examiner*—Moshe I. Cohen
*Attorney, Agent, or Firm*—Malin, Haley, McHale, DiMaggio & Crosby

[57] ABSTRACT

A brace is provided for localized immobilization of parts of the living body whereby the supports are conformable to the immobilized areas, and healing may be observed. The method of application includes heating preforms to a condition of plasticity and conforming them to the area requiring bracing.

2 Claims, 2 Drawing Sheets

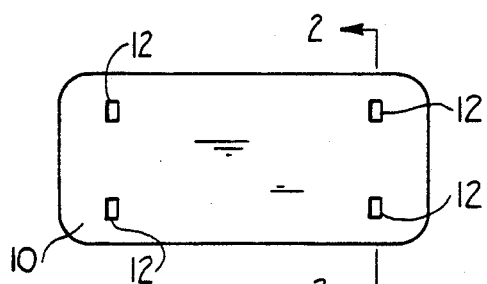
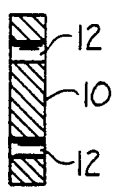
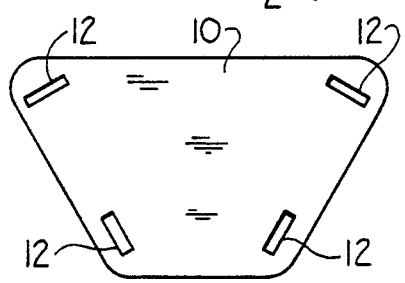
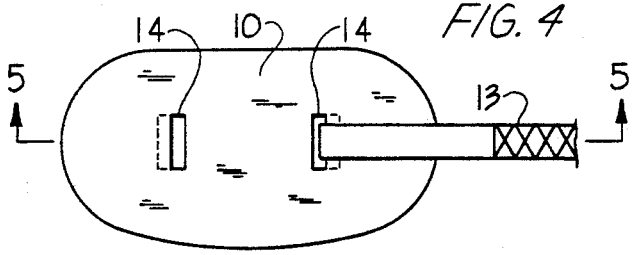
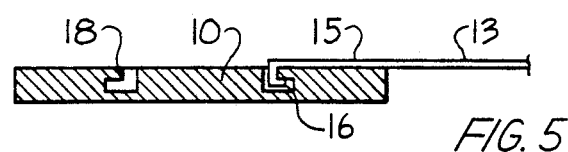
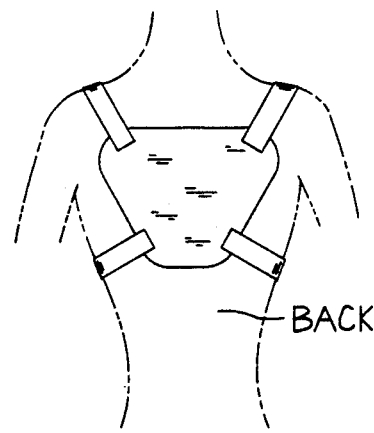
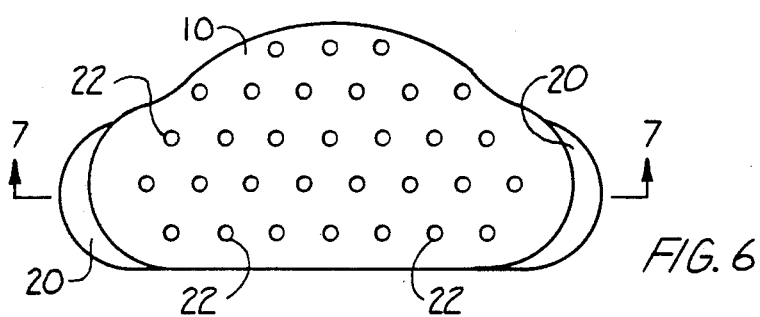
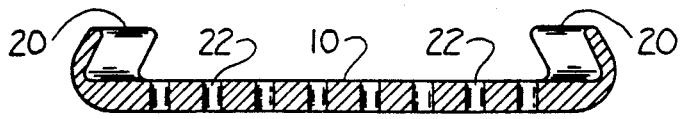

CONFORMABLE BRACE AND METHOD OF APPLICATION

This application is a continuation of application Ser. No. 07/562,451, filed Aug. 1, 1990 now abandoned, which is a continuation of Ser. No. 07/210,325, filed June 23, 1989, now abandoned.

BACKGROUND OF THE INVENTION

The present invention relates to a brace primarily intended for localized immobilization of parts of the human body during treatment, and methods of facile application of the brace by the healing arts and related sciences.

Presently, when a sprain or fracture requires that movement of a member or muscle area be restricted for a prolonged period, casts or girdles have been the treatment of choice. While providing the support and stability required, these means are awkward, and time consuming to apply. They obscure the healing process for the physician, and create discomfort for the wearer. They limit the patient's activities, because they may not be immersed and are heavy or cumbersome. A serious drawback is their interference with application of medication to the covered site. Girdles and bindings confine more of the body than is medically necessary.

BRIEF SUMMARY OF THE INVENTION

An object of this invention is to provide a conformable support for injured parts of the body. Conformation is preferable to binding and squeezing because it is less constrictive of blood circulation and permits the patient to function more closely to normal when areas adjacent to the injury are not immobilized.

A further object is to afford a light weight support. Present casting and bracing, for instance, are heavy and awkward that the patient is discouraged from following his/her normal pursuits.

Another object of the invention is to provide facility in application. Casts, bindings and girdles are traumatic to apply to the injured member because of the manipulation and time required to install them. This adds to the patient's pain and discomfort.

Yet another object is to provide a brace that is easy to fasten and to remove for cleaning, debriding and applying medication.

Still another object is to afford transparency for observation of the progress of healing of the injury.

A further object is to provide an immersible brace that does not deteriorate when the immobilized member is submerged, as in a whirlpool bath and to provide thermotherapeutic transmission of heat or cold without removal of the brace.

Another object is to provide a facile method of application of these braces to the injured body.

Other objects will become apparent from the illustrative embodiments described. Advantages not referred to herein will occur to one skilled in the art upon employment of the invention in practice.

BRIEF DESCRIPTION OF THE DRAWINGS

FIG. 1 is a plan view of the first embodiment of this invention.

FIG. 2 is a cross-sectional view taken along 2—2 of FIGS. 1 and 3.

FIG. 3 is a plan view of a second embodiment of the invention.

FIG. 4 is a plan view of another embodiment of the invention.

FIG. 5 is a cross-sectional view taken along section 5—5 of FIG. 4.

FIG. 6 is a plan view of an embodiment with perforations and engagement projections.

FIG. 7 is a cross-sectional view taken along section 7—7 of FIG. 6.

FIG. 8 is a conceptual drawing showing the application of the invention to the lower back.

FIG. 9 is a conceptual illustration showing an application of the embodiment of the invention of FIG. 3 to the upper back.

DETAILED DESCRIPTION OF THE INVENTION

The brace of this invention comprises a pair of plastic members adapted to be worn against opposite sides of the body part to be immobilized. A first pre-formed support blank in FIG. 1 comprises a flat plate 10 of transparent plastic material such as acrylic having rigidity at any desired temperature, for instance below 120° F. or at a higher temperature as desired. Plasticity will exist at a temperature well above 100° F. and preferably above 220° F. Preferably the plastic acrylic material becomes soft and deformable at temperatures above 220° Fahrenheit. The plastic material becomes rigid as it cools, and for instance, can become rigid at temperatures of 180° or less. Dupont's LUCITE brand has been found to be an excellent acrylic for obtaining the above results. Although acrylics are the preferred material for the blanks 10 in the instant invention, any other material which is able to reach the plasticity at temperatures above 120° F. and a state of rigidity at temperatures below 120° F. is well within the scope of the invention. Slots 12 penetrate the blank and afford engagement with flexible fastening means such as straps. A thin sheet of insulating material such as a quilted cloth or towel is placed upon the part of the body to be immobilized, say the small of the back. Although a cotton towel or cloth is the preferred insulating material for the instant invention, any other source of insulation which will not melt or destruct at temperatures above 120° F. is within the scope of the invention. Additionally, any object of cotton, polyester, rayon, silicon, rubber, or any other material, which will protect the skin from the high temperatures of the heated blanks 10 may also be used. These examples are merely exemplary and not intended to be limiting. The important thing is that the insulated material protect the skin from the high temperatures of the heated blanks 10.

Figure 11:
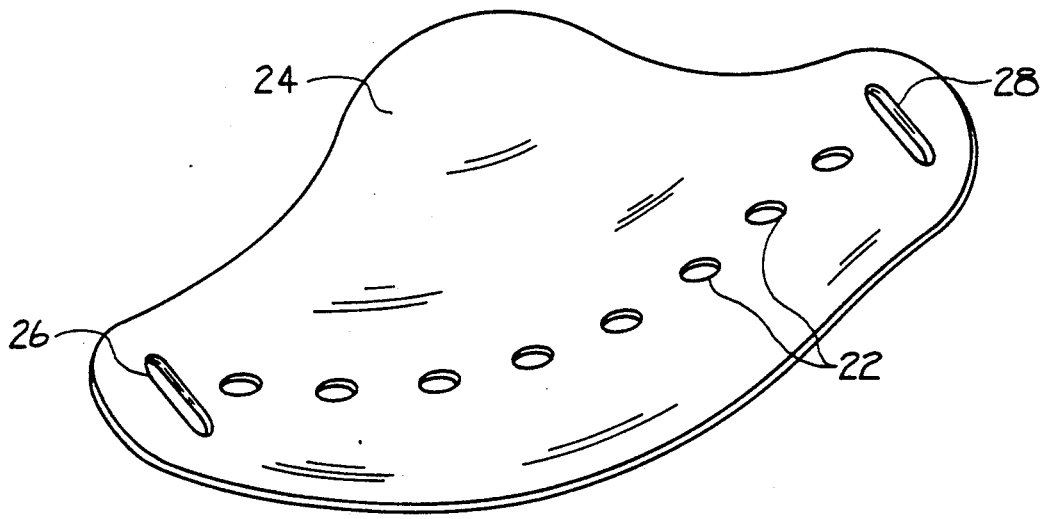
FIG. 11 is a perspective view of the brace member of FIG. 10 in softened form.

The acrylic pre-form is heated to plasticity in an oven or on a hot plate, and removed to the insulating cloth, which protects the skin from the sudden discomforting touch of the heated blank. The hot plate may be heated to approximately 300° Fahrenheit and is removed from the hot plate in its softened state as shown in FIG. 11. Pressure is applied against the positioned softened blank to make it conform to the contour of the patient's back and is released when the blank has cooled sufficiently to harden and maintain the shape that conforms to the patient's back. This will normally take between three and seven minutes.

The blank 10 and insulation are then removed, and holding straps are engaged with the slots 12. The conformed blank is replaced at the site of the injury, and the straps brought around and joined at the front of the body. As the straps are tightened, the plate applies uniform immobilizing pressure to the localized area of the back that required immobilization.

An alternative more specific method of forming the conformed blank is to place the heated soft deformable blank in that state in an insulated pocket which is then placed against the body part. A VELCRO ® strap is placed around the body to hold the heated blank against the body while pressure is directly applied thereto to conform the cooling acrylic plastic to the surface of the body part being supported. After the plate is cooled, it is removed from the insulated pocket and directly applied to the body part by suitable support straps.

An opposite plastic plate is similarly conformed and used on the front of the body, and thereby permit the use of pre-sized straps 13. Such straps can be installed even more quickly when they are provided with end hooks 15 that engage in slots 14 configured with undercuts 16 that create engagement tabs 18 illustrated in FIGS. 4 and 5. A plurality of undercut slots selectively spaced would allow precise incremental adjustment of pressure on the injured area. An articulating member of the body, such as an elbow or finger might require more than one opposing plate, if it must be immobilized in a bent position.

The transparency of the pressure plate is particularly useful when surface healing of a wound must be monitored. Furthermore, during the initial fitting, if it is seen that if conformity is lacking, the pre-form may be removed, reheated to plasticity, and reapplied, all in less time than with conventional supports, and with less distress to the patent. The simplicity of the method even makes it practical for use at the site of an accident, before a patient is moved to an ambulance or hospital.

In the embodiments of FIGS. 6 and 7, the ends of the pre-formed plates are bent to provide fastening means 20. Also shown are a plurality of perforations 22 which allow exposure of the covered area to air or to liquid such as medication. Because the transparent material is waterproof and impact resistant, the patient may participate in therapeutic activities like whirlpool baths. In situations requiring ice packs, the acrylic material is sufficiently thermoconducting to cool the specific area.

Figure 10:
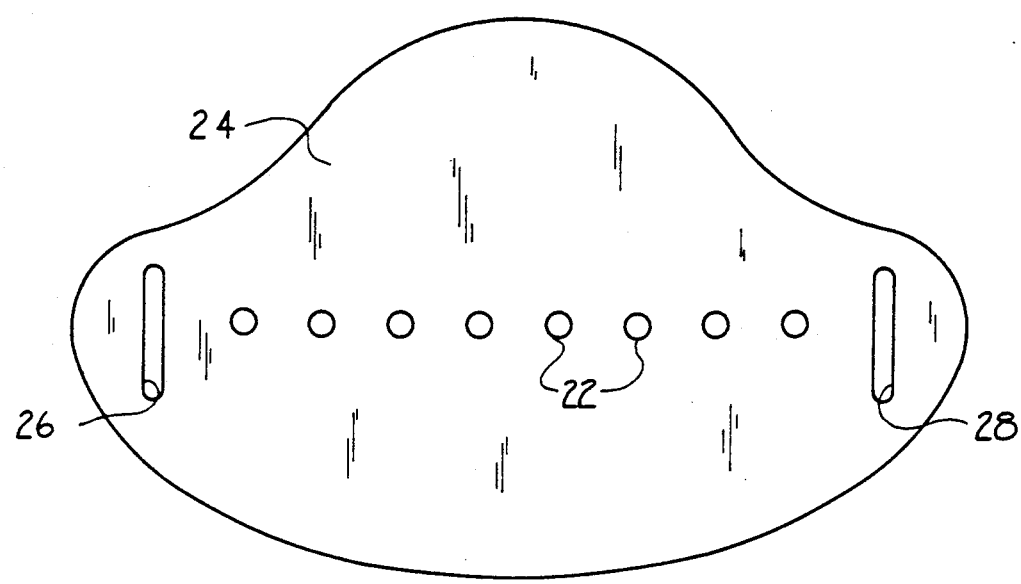
FIG. 10 is a plan view of another shape for a brace member.

The opposing plate may be formed in the same shape as that of plate 24 shown in FIG. 10. The support and opposing plates are each separately heated to take the soft shape in FIG. 11 and conform to the opposite body parts to be supported. After the opposite plates cool and become rigid, a strap passes through outer slots 26 and 28 of plate 24 and passes around the outer surfaces of the plates to draw the plates against the respective body parts. The strap may be adjustably closed by VELCRO or other adjustable fastening means.

The invention may be applied to any part of the muscular-skeletal system of the body that needs immobilization. Because it is molded and conformed to specific areas of treatment, the invention releases unaffected areas for free and normal body movements.

These conformed blanks may also be used for muscle toning by wearing them regularly. The isometric pressure which is created between the plate and held body part contributes to muscle tone and strength and helps a patient's rehabilatory processes. Using pairs of opposed plates provides the desired muscle toning.

As many apparently widely different embodiments of the present invention may be made without departing from the spirit and scope thereof, it is to be understood that the invention is not limited to the specific embodiments described herein except as defined in the appended claims.

What is claimed is:

1. A method of immobilizing a body part, comprising the steps of:
   (a) placing a thin sheet of heat insulating material upon said body part to be immobilized;
   (b) heating a first of a plurality of pre-formed plastic blanks of transparent material above 120° F. to a condition of plasticity;
   (c) removing said first plastic blank from the heat source and placing it against the exposed surface of said insulating material;
   (d) applying pressure against said first plastic blank and conforming it to the shape of said body part to be immobilized;
   (e) maintaining the conforming pressure until said first plastic blank has cooled to a temperature at which said first plastic blank becomes rigid and retains the conformation to the contour of said body part to be immobilized;
   (f) removing said first blank and insulating material from said body part;
   (g) repeating steps (a) through (f) for the remaining preformed plastic blanks;
   (h) placing said conformed blanks against opposite sides of said body part and securing them in position to immobilize said body part.

2. The method of claim 1, further comprising the step of securing said blanks to said body part as said blanks are cooling with VELCRO strap members.

* * * * *